(12) United States Patent
Madhani

(10) Patent No.: US 10,015,626 B2
(45) Date of Patent: *Jul. 3, 2018

(54) GEOSPATIAL-BASED DETECTION OF MOBILE COMPUTING DEVICE MOVEMENT

(71) Applicant: FMR LLC, Boston, MA (US)

(72) Inventor: Sunil Madhani, Cary, NC (US)

(73) Assignee: FMR LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,564

(22) Filed: May 26, 2017

(65) Prior Publication Data

US 2017/0332193 A1    Nov. 16, 2017

Related U.S. Application Data

(63) Continuation of application No. 15/155,041, filed on May 15, 2016, now Pat. No. 9,686,644.

(51) Int. Cl.
| | |
|---|---|
| *H04W 4/02* | (2018.01) |
| *H04W 4/021* | (2018.01) |
| *H04W 4/14* | (2009.01) |
| *G01N 19/10* | (2006.01) |
| *G01C 5/06* | (2006.01) |
| *G06F 21/31* | (2013.01) |
| *G01S 19/16* | (2010.01) |
| *G01S 19/42* | (2010.01) |
| *G01S 19/45* | (2010.01) |
| *G01L 19/12* | (2006.01) |

(52) U.S. Cl.
CPC ............. *H04W 4/02* (2013.01); *G01C 5/06* (2013.01); *G01L 19/12* (2013.01); *G01N 19/10* (2013.01); *G01S 19/16* (2013.01); *G01S 19/42* (2013.01); *G01S 19/45* (2013.01); *G06F 21/31* (2013.01); *H04W 4/14* (2013.01)

(58) Field of Classification Search
CPC ....... H04W 4/005; H04W 48/08; H04W 4/21; H04W 4/02
USPC .......................... 455/411, 418, 456.1, 456.3
See application file for complete search history.

(56) References Cited

U.S. PATENT DOCUMENTS

| | | | |
|---|---|---|---|
| 6,246,862 | B1 | 6/2001 | Grivas et al. |
| 6,744,403 | B2 | 6/2004 | Milnes et al. |

(Continued)

*Primary Examiner* — William D Cumming
(74) *Attorney, Agent, or Firm* — Proskauer Rose LLP

(57) ABSTRACT

Methods, systems and apparatuses, including computer program products, are described for detecting movement of a mobile computing device based upon geospatial data about a property location of the mobile computing device. The mobile computing device generates a baseline geospatial profile including baseline altitude data, baseline pressure data, and a predetermined pressure range. The mobile computing device enters a first operational mode permitting a user to establish a user session on the mobile computing device. The mobile computing device obtains altitude data from a first sensor and pressure data from a second sensor, and generates a geospatial signature based upon the altitude data and the pressure data. The mobile computing device compares the geospatial signature and the baseline geospatial profile, and enters a second operational mode if a difference between one or more corresponding values of the baseline geospatial profile and the geospatial signature exceeds a predetermined threshold.

20 Claims, 4 Drawing Sheets

(56) References Cited

U.S. PATENT DOCUMENTS

| | | | |
|---|---|---|---|
| 7,380,000 B2 | 5/2008 | Yaqub et al. | |
| 7,891,103 B2 | 2/2011 | Mayor et al. | |
| 8,265,871 B1* | 9/2012 | Starns | G06F 17/3087 455/456.3 |
| 8,467,779 B2* | 6/2013 | Helfrich | H04L 67/125 455/420 |
| 8,655,027 B1 | 2/2014 | Olthoff | |
| 8,682,309 B2* | 3/2014 | Helfrich | H04L 67/125 455/420 |
| 9,066,211 B2* | 6/2015 | Helfrich | H04L 67/125 |
| 9,232,354 B2 | 1/2016 | Smith | |
| 9,253,602 B2 | 2/2016 | Smith | |
| 9,332,386 B2 | 5/2016 | Smith | |
| 9,344,848 B2 | 5/2016 | Smith | |
| 9,554,323 B2* | 1/2017 | Banks | H04W 48/08 |
| 9,686,644 B1* | 6/2017 | Madhani | H04W 4/02 |
| 9,686,646 B1* | 6/2017 | Pecard | H04W 4/021 |
| 9,736,368 B2* | 8/2017 | Lablans | H04N 5/23238 |
| 9,743,236 B1* | 8/2017 | Pecard | H04W 4/021 |
| 2003/0091215 A1 | 5/2003 | Lauper et al. | |
| 2004/0172562 A1 | 9/2004 | Berger et al. | |
| 2005/0008148 A1 | 1/2005 | Jacobson | |
| 2007/0016088 A1 | 1/2007 | Grant et al. | |
| 2007/0218823 A1 | 9/2007 | Wolf | |
| 2007/0218891 A1 | 9/2007 | Cox | |
| 2009/0133106 A1 | 5/2009 | Bentley et al. | |
| 2010/0229192 A1 | 9/2010 | Marilly et al. | |
| 2010/0328074 A1 | 12/2010 | Johnson et al. | |
| 2011/0039522 A1 | 2/2011 | Partridge et al. | |
| 2011/0054776 A1* | 3/2011 | Petrov | G01C 21/3694 701/533 |
| 2011/0159850 A1 | 6/2011 | Faith et al. | |
| 2011/0274318 A1 | 11/2011 | Shindo et al. | |
| 2012/0088210 A1 | 4/2012 | Batcheller et al. | |
| 2012/0149353 A1* | 6/2012 | Helfrich | H04L 67/125 455/418 |
| 2012/0254740 A1 | 10/2012 | Levien et al. | |
| 2013/0040600 A1 | 2/2013 | Reitnour et al. | |
| 2013/0045759 A1 | 2/2013 | Smith | |
| 2013/0157607 A1 | 6/2013 | Paek et al. | |
| 2013/0157718 A1 | 6/2013 | Johanson et al. | |
| 2013/0252586 A1* | 9/2013 | Helfrich | H04L 67/125 455/411 |
| 2014/0025973 A1 | 1/2014 | Schillings et al. | |
| 2014/0087707 A1 | 3/2014 | Gustafsson et al. | |
| 2014/0155087 A1* | 6/2014 | Helfrich | H04L 67/125 455/456.1 |
| 2014/0171068 A1 | 6/2014 | Marti et al. | |
| 2014/0187256 A1 | 7/2014 | Modali et al. | |
| 2014/0188638 A1 | 7/2014 | Jones et al. | |
| 2014/0196119 A1 | 7/2014 | Hill et al. | |
| 2014/0236644 A1 | 8/2014 | Abhyanker | |
| 2014/0243020 A1 | 8/2014 | Lerene | |
| 2014/0267775 A1* | 9/2014 | Lablans | H04N 5/247 348/169 |
| 2014/0273920 A1 | 9/2014 | Smith | |
| 2014/0289821 A1 | 9/2014 | Wilson | |
| 2015/0082421 A1 | 3/2015 | Flowers et al. | |
| 2015/0135284 A1 | 5/2015 | Bogard | |
| 2015/0139082 A1* | 5/2015 | Banks | H04W 48/08 370/329 |
| 2015/0341756 A1 | 11/2015 | Heshmati et al. | |
| 2015/0350836 A1 | 12/2015 | Smith | |
| 2015/0350837 A1 | 12/2015 | Smith | |
| 2015/0381609 A1 | 12/2015 | Dadu et al. | |
| 2016/0029224 A1 | 1/2016 | Edge | |
| 2016/0094949 A1 | 3/2016 | Smith | |
| 2016/0129913 A1 | 5/2016 | Boesen | |
| 2016/0182503 A1 | 6/2016 | Cheng et al. | |
| 2016/0212581 A1 | 7/2016 | Smith | |
| 2017/0094698 A1* | 3/2017 | Banks | H04W 48/08 |
| 2017/0323458 A1* | 11/2017 | Lablans | G06T 7/73 |
| 2017/0332193 A1* | 11/2017 | Madhani | H04W 4/02 |

* cited by examiner

300

305 Generating a baseline geospatial profile comprising baseline altitude data, baseline pressure data, and a predetermined pressure range 310 Entering a first operational mode, wherein the first operational mode permits a user to establish a user session on the mobile computing device 315 Obtaining altitude data from a first sensor responsive to a change in altitude of the mobile computing devices 320 Obtaining pressure data from a second sensor responsive to a change in a pressure of the location of the mobile computing device 325 Generating a geospatial signature based upon the altitude data and the pressure data 330 Generating one or more computer-executable statements for joining the filtered storage system data tables into a joined table based on the join sequence 335 Comparing the geospatial signature and the baseline geospatial profile 340 Entering a second operational mode if a difference between one or more corresponding values of the baseline geospatial profile and the geospatial signature exceeds a predetermined threshold

405 Generating a baseline proximity profile, wherein the baseline proximity profile comprises data corresponding to at least three properties of a location of the mobile computing device 410 Enter a first operational mode, wherein the first operational mode permits a user to establish a user session on the mobile computing device 415 Obtaining first sensor data from a first sensor responsive to a first property of the location of the mobile computing device 420 Obtaining second sensor data from a second sensor responsive to a second property of the location of the mobile computing device 425 Obtaining third sensor data from a third sensor responsive to a third property of the location of the mobile computing device, wherein the first, second, and third properties are different 430 Generating a proximity signature based upon the first sensor data, the second sensor data, and the third sensor data 435 Compare the geospatial signature and the baseline geospatial profile 440 Entering a second operational mode if a difference between one or more corresponding values of the baseline proximity profile and the proximity signature exceeds a predetermined threshold

FIG. 4

GEOSPATIAL-BASED DETECTION OF MOBILE COMPUTING DEVICE MOVEMENT

CROSS REFERENCE TO RELATED APPLICATION

This application is a continuation of U.S. patent application Ser. No. 15/155,041, filed May 15, 2016, now U.S. Pat. No. 9,686,644, which is hereby incorporated by reference herein in its entirety.

TECHNICAL FIELD

This application relates generally to systems, methods and apparatuses, including computer program products, for detecting movement of a mobile computing device based upon geospatial data about a property location of the mobile computing device.

BACKGROUND

Today's mobile computing devices, such as tablets and smartphones, are designed to be portable and lightweight, yet still have ample processing power for handling the processing demands of commonly-used software applications. As a result, many business locations such as kiosks and retail stores use mobile computing devices to facilitate business transaction with customers. For example, a customer of a wireless carrier may visit the carrier's retail store because they are interested in upgrading their phone or changing their phone plan. Using a mobile computing device at the wireless carrier's retail store location, the customer can log into their account to look up their existing plan and billing information, discuss and compare their plan options with a sales representative while simultaneously viewing new smartphones throughout the store, and authorize changes to their account immediately upon making a decision.

However, the usefulness and portability of mobile computing devices also makes them popular targets for thieves who can easily slip them into a backpack or small bag undetected and carry them out of the retail store. The loss resulting from a stolen mobile computing device is twofold. Clearly, the business owner suffers a financial loss from having to replace the stolen device. However, a far greater loss can be suffered if the thief is able to obtain and use the business owner's sensitive or confidential information that may be stored on the mobile computing device. Further, there is a similar risk of loss to a customer who may have been logged into the mobile computing device at the time it was taken.

Current systems and methods for preventing theft of mobile computing devices seek to solve the problem by attaching the mobile computing device to one end of a wire or cable "tether" while the other end is anchored to some stationary object within the retail store (e.g., desk, display table). However, this approach is cumbersome and undesirable because it limits one of the most useful aspects of the mobile computing device: its portability. Further, many business owners have labored to build a brand and reputation with their customers that is based on a mutual trust, and tethering calls that trust into question in the minds of their customers.

Some businesses have certain legal, regulatory and compliance requirements related to inactivity logouts of user sessions operating on a mobile computing device. For example, one such requirement may mandate that an inactive user session is logged out after no more than 180 seconds of inactivity. However, such timeouts leaves ample time for a thief to swipe a mobile computing device on which a customer's user session has been established and make it out of the retail store location before the inactivity timeout occurs, allowing the thief to maintain the user session and accordingly gain access the customer's account and personal information.

SUMMARY

Accordingly, there is a need for improved methods and systems for monitoring the movement of mobile computing devices, and for protecting sensitive and confidential information stored on mobile computing devices and displayed on mobile computing devices during user sessions.

The invention, in one aspect, features a computerized method for detecting movement of a mobile computing device based upon geospatial data about a property location of the mobile computing device. A mobile computing device generates a baseline geospatial profile including baseline altitude data, baseline pressure data, and a predetermined pressure range. The mobile computing device enters a first operational mode, where the first operational mode permits a user to establish a user session on the mobile computing device. The mobile computing device obtains altitude data from a first sensor responsive to a change in altitude of the mobile computing device, and obtains pressure data from a second sensor responsive to a change in a pressure of the location of the mobile computing device. The mobile computing device generates a geospatial signature based upon the altitude data and the pressure data. The mobile computing device compares the geospatial signature and the baseline geospatial profile, and enters a second operational mode if a difference between one or more corresponding values of the baseline geospatial profile and the geospatial signature exceeds a predetermined threshold.

The invention, in another aspect, features a computer program product, tangibly embodied in a non-transitory computer readable storage device, for detecting movement of a mobile computing device based upon geospatial data about a property location of the mobile computing device. The computer program product includes instructions operable to cause the mobile computing device to generate a baseline geospatial profile including baseline altitude data, baseline pressure data, and a predetermined pressure range. The computer program product includes instructions operable to cause the mobile computing device to enter a first operational mode, where the first operational mode permits a user to establish a user session on the mobile computing device. The computer program product includes instructions operable to cause the mobile computing device to obtain altitude data from a first sensor responsive to a change in altitude of the mobile computing device. The computer program product includes instructions operable to cause the mobile computing device to obtain pressure data from a second sensor responsive to a change in a pressure of the location of the mobile computing device. The computer program product includes instructions operable to cause the mobile computing device to generate a geospatial signature based upon the altitude data and the pressure data. The computer program product includes instructions operable to cause the mobile computing device to compare the geospatial signature and the baseline geospatial profile. The computer program product includes instructions operable to cause the mobile computing device to enter a second operational mode if a difference between one or more corresponding values of the baseline geospatial profile and the geospatial signature exceeds a predetermined threshold.

Any of the above aspects can include one or more of the following features. In some embodiments, generating the baseline geospatial profile further includes: obtaining, by the mobile computing device, GPS coordinate data from a GPS of the mobile computing device, where the GPS coordinate data corresponds to a geographic location of the mobile computing device prior to entering the first operational mode; determining, by the mobile computing device, a property location of the mobile computing device based upon the GPS coordinate data; retrieving, by the mobile computing device, the predetermined altitude threshold from a server computing device based upon the property location of the mobile computing device; obtaining, by the mobile computing device, the baseline pressure data from the second sensor prior to entering the first operational mode; and retrieving, by the mobile computing device, the predetermined pressure range from a server computing device, where the predetermined pressure range comprises a maximum pressure value and a minimum pressure value.

In some embodiments, the predetermined pressure range is based upon historical pressure data corresponding to the property location of the mobile computing device retrieved from a server computing device. In some embodiments, the predetermined pressure range is based upon currently-forecasted pressure data corresponding to the property location of the mobile computing device retrieved from a server computing device.

In some embodiments, entering the second operational mode further includes determining, by the mobile computing device, whether the pressure data is outside of the predetermined pressure range if one or more of: (i) a difference between the baseline altitude data and the altitude data exceeds a first predetermined threshold, and (ii) a difference between the baseline pressure data and the pressure data exceeds a second predetermined threshold. In some embodiments, entering the second operational mode further includes entering, by the mobile computing device, the second operation mode if the pressure data is outside of the predetermined pressure range. In some embodiments, the mobile computing device determines if the difference between the baseline altitude data and the altitude data exceeds a first predetermined threshold when the altitude data is less than the baseline altitude data In some embodiments, the first sensor is an altimeter. In some embodiments, the second sensor is a hygrometer.

In some embodiments, entering the second operational mode includes one or more of: transmitting, by the mobile computing device, an alert to a remote computing device; locking, by the mobile computing device, a user session that has been established on the mobile computing device; ending, by the mobile computing device, a user session that has been established on the mobile computing device; generating, by the mobile computing device, an audible alarm on a speaker of the mobile computing device; generating, by the mobile computing device, a visual alarm on one or more of a display and a light source of the mobile computing device; prompting, by the mobile computing device, the user to enter user credential information; or erasing, by the mobile computing device, the contents of a volatile and a non-volatile information storage of the mobile computing device.

In some embodiments, the alert includes one or more of: a unique device identifier of the mobile computing device, a time stamp indicating when the mobile computing device entered the second operational mode, the altitude data, and the pressure data. In some embodiments, transmitting the alert further includes formatting, by the mobile computing device, the alert for transmission as one or more of an SMS message, an instant message according to the IMESSAGE protocol, and an email.

The invention, in another aspect, features a computerized method for detecting proximity of a mobile computing device based upon physical properties of a property location of the mobile computing device. The mobile computing device generates a baseline proximity profile, where the baseline proximity profile includes data corresponding to at least three properties of a location of the mobile computing device. The mobile computing device enters a first operational mode, where the first operational mode permits a user to establish a user session on the mobile computing device. The mobile computing device obtains first sensor data from a first sensor responsive to a first property of the location of the mobile computing device. The mobile computing device obtains second sensor data from a second sensor responsive to a second property of the location of the mobile computing device. The mobile computing device obtains third sensor data from a third sensor responsive to a third property of the location of the mobile computing device, where the first, second, and third properties are different. The mobile computing device generates a proximity signature based upon the first sensor data, the second sensor data, and the third sensor data. The mobile computing device enters a second operational mode if a difference between one or more corresponding values of the baseline proximity profile and the proximity signature exceeds a predetermined threshold.

The invention, in another aspect, features a computer program product, tangibly embodied in a non-transitory computer readable storage device, for detecting a proximity of a mobile computing device based upon physical properties of a property location of the mobile computing device. The computer program product includes instructions operable to cause the mobile computing device to generate a baseline proximity profile, where the baseline proximity profile comprises data corresponding to at least three properties of a location of the mobile computing device. The computer program product includes instructions operable to cause the mobile computing device to enter a first operational mode, where the first operational mode permits a user to establish a user session on the mobile computing device. The computer program product includes instructions operable to cause the mobile computing device to obtain first sensor data from a first sensor responsive to a first property of the location of the mobile computing device. The computer program product includes instructions operable to cause the mobile computing device to obtain second sensor data from a second sensor responsive to a second property of the location of the mobile computing device. The computer program product includes instructions operable to cause the mobile computing device to obtain third sensor data from a third sensor responsive to a third property of the location of the mobile computing device, where the first, second, and third properties are different. The computer program product includes instructions operable to cause the mobile computing device to generate a proximity signature based upon the first sensor data, the second sensor data, and the third sensor data. The computer program product includes instructions operable to cause the mobile computing device to enter a second operational mode if a difference between one or more corresponding values of the baseline proximity profile and the proximity signature exceeds a predetermined threshold.

Any of the above aspects can include one or more of the following features. In some embodiments, generating the proximity signature further includes determining, by the mobile computing device, a luminance based upon the third sensor data, and generating, by the mobile computing device, a proximity signature data structure comprising the first sensor data, the second sensor data, and the luminance.

In some embodiments, generating the baseline proximity profile further includes: obtaining, by the mobile computing device, first baseline data from the first sensor; obtaining, by the mobile computing device, second baseline data from the second sensor; obtaining, by the mobile computing device, third baseline data from the third sensor; determining, by the mobile computing device, a baseline luminance based upon the third baseline data; and generating, by the mobile computing device, a baseline proximity profile data structure comprising the first baseline data, the second baseline data, and the baseline luminance.

In some embodiments, entering the second operational mode further includes determining, by the mobile computing device, a difference between the first baseline data and the first sensor data, and, if the difference between the first baseline data and the first sensor data exceeds a first predetermined threshold: determining, by the mobile computing device, a difference between the second baseline data and the second sensor data; determining, by the mobile computing device, a difference between the baseline luminance and the luminance; and entering, by the mobile computing device, the second operational mode. In some embodiments, the mobile computing device enters the second operational mode when at least one of the difference between the second baseline data and the second sensor data exceeds a second predetermined threshold, and the difference between the baseline luminance and a luminance calculated based upon the third sensor data exceeds a third predetermined threshold.

In some embodiments, the first sensor is a magnetometer, and the first property of the location of the mobile computing device is a strength of a magnetic field. In some embodiments, the second sensor is a sound transducer, and the second property of the location of the mobile computing device comprises one or more of a sound amplitude, a sound tone, and a sound pitch. In some embodiments, the third sensor is a light sensor, and the third property of the location of the mobile computing device comprises a plurality of wavelengths of light.

In some embodiments, entering the second operational mode comprises one or more of: transmitting, by the mobile computing device, an alert to a remote computing device; locking, by the mobile computing device, a user session that has been established on the mobile computing device; ending, by the mobile computing device, a user session that has been established on the mobile computing device; generating, by the mobile computing device, an audible alarm on a speaker of the mobile computing device; generating, by the mobile computing device, a visual alarm on one or more of a display and a light source of the mobile computing device; prompting, by the mobile computing device, the user to enter user credential information; or erasing, by the mobile computing device, the contents of a volatile and a non-volatile information storage medium of the mobile computing device.

In some embodiments, the alert comprises one or more of a device identifier of the mobile computing device, a time stamp indicating when the mobile computing device entered the second operational mode, the first sensor data, the second sensor data, and a luminance calculated based upon the third sensor data. In some embodiments, transmitting the alert further comprises formatting the alert for transmission as one or more of an SMS message, an instant message according to the IMESSAGE protocol, and an email.

Other aspects and advantages of the invention will become apparent from the following detailed description, taken in conjunction with the accompanying drawings, illustrating the principles of the invention by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 3 is a flow diagram of a method for detecting movement of a mobile computing device based upon geo-spatial data about a property location of the mobile computing device in accordance with the invention.

FIG. 4 is a flow diagram of a method for detecting proximity of a mobile computing device based upon physical properties of a property location of the mobile computing device, in accordance with the invention.

DETAILED DESCRIPTION

Figure 1:
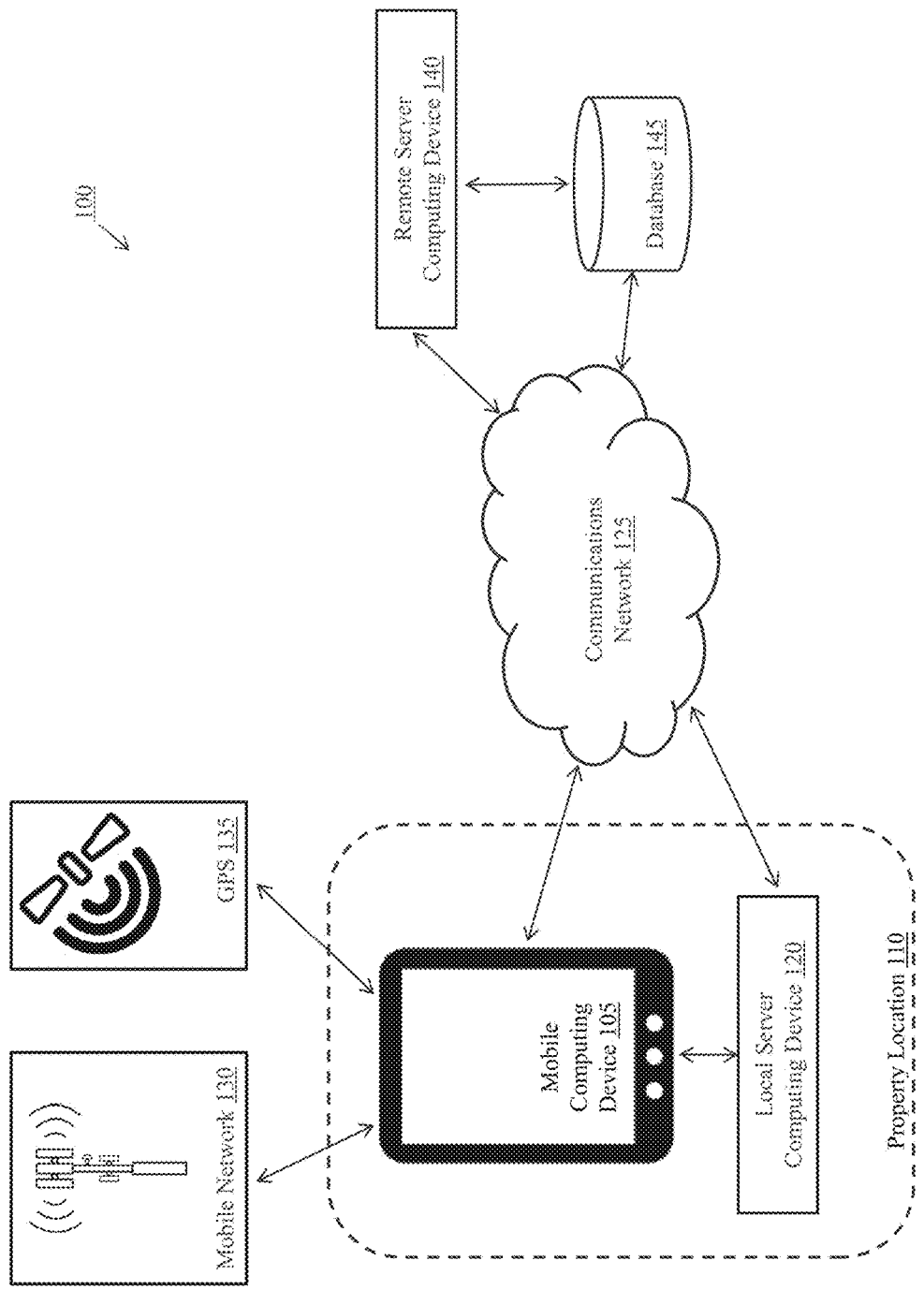
FIG. 1 is a block diagram of an exemplary system, in accordance with the invention.

FIG. 1 is a block diagram of a system 100 in accordance with embodiments of the invention described herein. System 100 includes property location 110 which houses local server computing device 120 and mobile computing device 105. Property location 110 can be a retail store location (e.g., a "brick-and-mortar" business location). In some embodiments, property location 110 is a branch location of a services institution (e.g., wireless carrier, cable network operator, financial services firm). In some embodiments, property location 110 is a kiosk located at a mall or other shopping area. Local server computing device 120 can be collocated with mobile computing device 105 to store and provide data about property location 110. In some embodiments, local server computing device 120 includes files, applications, and scripts that can be accessed by or served to mobile computing device 105 via a near field or network connection. In some embodiments, local server computing device 120 is a computer terminal used by a representative of the business owner of property location 110, and provides access to an internal network (e.g., intranet) that is not accessible via mobile computing device 105.

Although FIG. 1 shows a single mobile computing device at property location 110, it should be understood that any number of mobile computing devices can be located at property location 110. Examples of mobile computing device 105 include tablet computers, smartphones, and other mobile computing devices known in the art. In some embodiments, mobile computing device 105 is a laptop computer.

Figure 2:
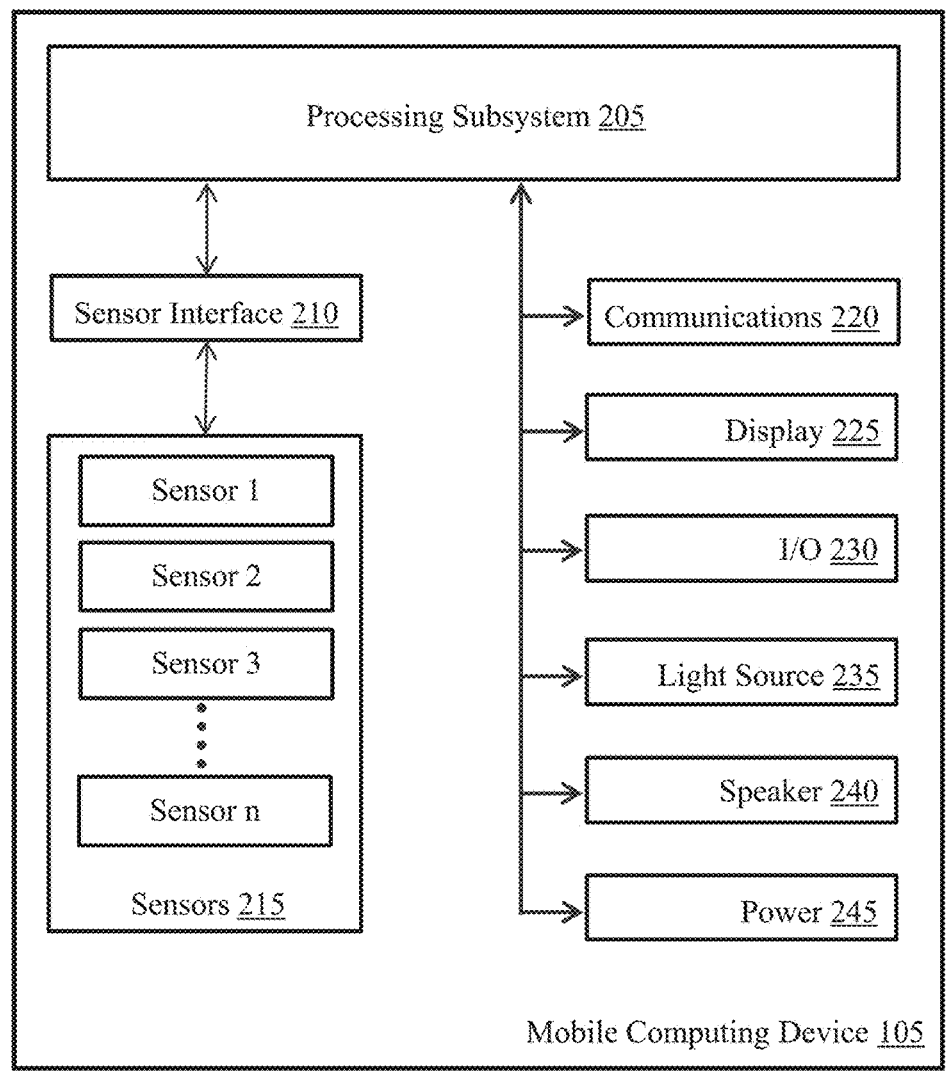
FIG. 2 is a block diagram of an exemplary mobile computing device, in accordance with the invention.

FIG. 2 is a block diagram 200 of an exemplary embodiment of mobile computing device 105. Mobile computing device 105 includes processing subsystem 205 in communication with sensor interface 210 for accessing a variety of sensors 215. Processing subsystem 205 generally includes a processor, volatile and non-volatile memory, and other logic for managing and interfacing with other components of mobile computing device 105. Processing subsystem 205 is programmed with computer software instructions enabling it to perform the computations and operations described herein in conjunction with the other components of mobile computing device 105. Sensor interface 210 includes circuitry to facilitate access to sensors 215. In some embodiments, sensor interface 210 includes a co-processor in communication with one or more of sensors 215 for collecting and processing sensor data from sensors 215.

Sensors 215 can include a plurality of sensors for detecting and/or measuring properties of mobile computing device 105 and its location (e.g., property location 110), and providing corresponding output (e.g., electrical signal, optical signal). For example, sensors 215 can include sensors responsive to changes in the altitude of mobile computing device 105 (e.g., barometric pressure sensor, pressure altimeter, barometric altimeter). Sensors 215 can also include sensors responsive to a change in moisture content in the atmosphere (e.g., hygrometer), and sensors responsive to changes in the strength of a magnetic field (e.g., magnetometer, teslameter, gaussmeter). Sensors 215 can further include sensors responsive to changes in properties of sound (e.g., microphone, sound transducer) such as changes in the amplitude, tone, pitch, and/or duration of sound. In some examples, sensors 215 include sensors responsive to changes in properties of light (e.g. ambient light sensor, photodetector, phototransistor, photodetector) such as changes in intensity and wavelength.

In some embodiments, sensors 215 includes sensors responsive to a change in linear acceleration (e.g., accelerometer) and angular velocity (e.g., gyroscope), and the output from the sensors comprises signals or data corresponding to a single axis or a plurality of axes (e.g., 2-axis sensor, 3-axis sensor).

Sensors 215 can further include other sensors such as an images sensor (e.g., camera), temperature sensor (e.g., thermometer), and biometric sensor (e.g., fingerprint reader). In some embodiments, mobile computing device 105 includes a plurality of a given sensor type for making multi-channel "diversity" measurements of certain properties.

Processing subsystem 205 is further in communication with several other components and subsystems of mobile computing device 105 such as communications 220, display 225, I/O 230, light source 235, speaker 240, and power 245. Although the example in FIG. 2 shows a shared connection between processing subsystem 205 and all of the other components and subsystems of mobile computing device 105, it should be understood that any number of connections or interfaces can be used to connect processing subsystem 205 to the other components and subsystems different components.

Communications 220 includes circuitry to facilitate communications between mobile computing device 105 and other computing and peripheral devices using various protocols over various transmission mediums. For example, communications 220 can include circuitry for communicating using wireless technology (e.g., WiFi, cellular, GPS, Bluetooth) and wired technology (e.g., wired Ethernet, USB, optical, Lightning, FireWire). Display 225 can include a flat panel display (e.g., LCD display, OLED display) and associated circuitry for controlling the display of images on the display. In some embodiments, display 225 further includes a touch panel or touchscreen display as an input device to mobile computing device 105.

I/O 230 can include circuitry corresponding to one or more components for providing input to mobile computing device 105 (e.g., button, slider, switch), and providing output or feedback from mobile computing device 105 (e.g., audio signal output, video signal output, vibration circuit). Light source 235 can include one or more solid-state light sources (e.g., LED, OLED, PLED). In some embodiments, light source 235 includes components for enhancing or directing light from the solid state light source (e.g., reflector, lens, diffuser, light guide, light pipe) and/or circuitry for controlling the operation of light source 235. Speaker 240 can include one or more sound-producing components (e.g., speakers) and related components for enhancing or directing sound (e.g., resonance chamber, amplifier). Power 245 can include a battery for providing power to the various components of mobile computing device 105. Power 245 can also include circuitry for accepting power provided from a wired power source (e.g., AC/DC adapter, USB port), and charger circuitry for charging the battery.

Returning to FIG. 1, system 100 further includes communications network 125, mobile network 130, GPS satellites 135, remote server computing device 140 and database 145.

Communications network 125 facilitates data communications between the various components of system 100. Communications network 125 can be a local network, such as a LAN, or a wide area network ("WAN"), such as the Internet and/or a cellular network. Communications network 125 may alternatively comprise components of both a LAN and a WAN, or any other type of network known in the art.

In some embodiments, mobile computing device 105 includes connections to networks and systems independent of communications network 125 (e.g., mobile network 130, GPS satellites 135). In some embodiments, communications network 125 includes connections to network 130 and GPS satellites 135. In some embodiments, mobile computing device 105 and local server computing device 120 are in communication via a private network at property location 110. In some embodiments, mobile computing device 105 and local server computing device 120 are in communication using near field communications.

Database 145 is a computing device (or in some embodiments, a set of computing devices) coupled to remote server computing device 140 and accessible to mobile computing device 105 via communications with remote server computing device 140 or directly via communications network 125. In some embodiments, database 145 is configured to receive, generate, and store specific segments of data relating to the methods and systems described herein. In some embodiments, database 145 is repository for data relating to one or more property locations. In some embodiments, all or a portion of database 145 can be integrated with remote server computing device 140 or be located on a separate computing device or devices. Database 145 can comprise one or more databases configured to store portions of data used by the other components of the system 100. An exemplary database 145 is MySQL™ available from Oracle Corp. of Redwood City, Calif.

In some embodiments, remote server computing device 140 and database 145 are administered by a group associated with the business owner of property location 110 that manages the business owner's retail locations, and database 145 is a repository for data relating to aspects and properties of one or more of the business owner's property locations (e.g., property location 110).

FIG. 3 is a flow diagram of a method 300 for detecting movement of a mobile computing device based upon geospatial data about a property location of the mobile computing device, using the system 100 of FIG. 1. Mobile computing device 105 generates (305) a baseline geospatial profile comprising baseline altitude data, baseline pressure data, and a predetermined pressure range. In some embodiments, mobile computing device 105 generates a baseline geospatial profile at a predetermined interval (e.g., once per day, once per week). In some embodiments, mobile computing device 105 generates a geospatial proximity profile upon power up or restart of mobile computing device 105. In some embodiments, mobile computing device generates a baseline geospatial profile upon the termination of a user session.

To generate the baseline geospatial profile, mobile computing device 105 first uses the GPS circuitry of communications 220 to communicate with GPS satellites 135, and obtains GPS coordinate data corresponding to its geographic location (e.g., at property location 110).

Based upon the GPS coordinate data, mobile computing device 105 determines that it is located at property location 110, and retrieves a predetermined altitude threshold corresponding to the altitude of property location 110. For example, property location 110 can be one of several retail stores at which mobile computing device 105 can possibly be located, and each retail store can be located at a different altitude. Mobile computing device 105 can use the GPS coordinate data as a key or index to search a table stored in its memory that maps GPS coordinates to retail store property locations and their corresponding altitude data. In some embodiments, mobile computing device 105 formats the GPS coordinate data into a query submitted to at least one of local server computing device 120 or remote server computing device 140 which return a response including the predetermined altitude data corresponding to property location 110. In some embodiments, database 145 is a master database containing data about each property location at which there is a retail store, and the predetermined altitude data is retrieved from database 145 based upon the GPS coordinate data corresponding to property location 110.

In some embodiments, property location 110 is constructed according to municipal building codes or zoning regulations that require the floor level of the retail store at property location 110 to be a certain distance (e.g., number of steps) above ground level. The baseline altitude of the geospatial profile can be offset according to the distance the retail store at property location 110 is above ground level. For example, mobile computing device 105 can use such an offset in making computations related to altitude data received from sensors 215.

As part of generating the baseline geospatial profile, mobile computing device 105 obtains baseline pressure data from a pressure sensor of sensors 215. In some examples, the pressure sensor is a hygrometer responsive to changes in barometric pressure. Mobile computing device 105 also retrieves a predetermined pressure range to serve as the values to which subsequent samples of pressure are compared. The predetermined pressure range can correspond to a given time period (e.g., a certain month, a certain day) and location (e.g., a state, a town, a specific property location). The predetermined pressure range can include a minimum and a maximum pressure value corresponding to the day mobile computing device 105 retrieves the predetermined pressure range and its location when retrieving it. In some embodiments, mobile computing device 105 retrieves the predetermined pressure range from a network-connected server computing device storing current and historical pressure measurements. In some embodiments, mobile computing device 105 retrieves the predetermined pressure range from database 145 over communications network 125, or via an interaction with remote server computing device 140.

The predetermined pressure range can be based upon historical barometric pressure data for a particular property location for a given day. For example, based upon measurements from years past, the barometric pressure at a property located in Raleigh, N.C. on a given day in the month of May can range from 28 inHg and 31 inHg (approximately 970 hPa to 1500 hPa). In this case, the predetermined pressure range retrieved by mobile computing device 105 would include values to reflect a minimum pressure of 28 inHg and a maximum pressure of 31 inHg. In some embodiments, the predetermined pressure range is based upon the expected range of barometric pressure values indicated in a current forecast for property location 110. For example, a weather forecast for Raleigh, N.C. for the same day in May can include an expected barometric or atmospheric pressure range of between 29.95 inHg and 30.05 inHg.

In some embodiments, the pressure values of the predetermined pressure range represent pressure values measured outdoors, and the values of the predetermined pressure range are adjusted by an offset to reflect a known relative difference in pressure inside the retail store at property location 110 due to the operation of climate control systems (e.g., HVAC).

Mobile computing device 105 enters (310) a first operational mode, wherein the first operational mode permits a user to establish a user session on mobile computing device 105. For example, after generating the baseline geospatial profile, mobile computing device 105 can enter a mode in which a user is permitted to log into mobile computing device 105 with their user credentials and start using applications installed on mobile computing device 105.

Upon entering the first operational mode, mobile computing device 105 obtains (315) altitude data from a first sensor responsive to a change in altitude of the mobile computing device, and obtains (320) pressure data from a second sensor responsive to a change in a pressure of the location of the mobile computing device. In some examples, the first sensor is an altimeter. In some embodiments, mobile computing device 105 obtains altitude and pressure data from sensors 215 at predetermined intervals of time (e.g., every 3 seconds).

Mobile computing device 105 generates (325) a geospatial signature based upon the altitude data and the pressure data obtained at steps 315 and 320, respectively. The geospatial signature can be a data structure including the values for altitude and pressure obtained from the sensors. In some embodiments, the data values of the geospatial signature are formatted to facilitate comparison of the altitude and pressure values with values of the baseline geospatial profile. For example, the values of the geospatial signature can be formatted to use same degree of precision and units of measurement as the values in the baseline geospatial profile.

Mobile computing device 105 compares (330) the geospatial signature and the baseline geospatial profile, and enters (335) a second operational mode if a difference between one or more corresponding values of the baseline geospatial profile and the geospatial signature exceeds a predetermined threshold.

As part of the comparison, mobile computing device 105 determines if a difference between the baseline altitude data of the geospatial profile and the altitude data of the geospatial signature exceeds a first predetermined threshold. In some embodiments, determining if the difference between the baseline altitude data and the altitude data exceeds a first predetermined threshold includes determining that the altitude data of the geospatial signature is less than the baseline altitude data. For example, the first predetermined threshold is preferably set such that if mobile computing device 105 is removed from the retail store, the change in altitude caused by mobile computing device 105's descent down the retail store stairs to street level will cause the difference between the baseline altitude data of the geospatial profile and the altitude data of the geospatial signature to exceed the first predetermined threshold.

However, there is some ambiguity in the comparison due to the differing heights of users that may be holding and operating mobile computing device 105 within the retail store at property location 110, and also due to altitude differences caused by users that are sitting as opposed to standing, or even occasions when mobile computing device 105 is dropped during use. Accordingly, a determination that the difference between the baseline altitude data of the geospatial profile and the altitude data of the geospatial signature exceeds a first predetermined threshold is followed up with a comparison of the pressure data of the geospatial signature with the predetermined pressure range of the baseline geospatial profile as described in more detail below.

Mobile computing device 105 determines if a difference between the baseline pressure data of the geospatial profile and the pressure data of the geospatial signature exceeds a second predetermined threshold. For example, the second predetermined threshold can be based on a percent change in value (e.g., +/−5%) between the baseline pressure data of the geospatial profile and the pressure data of the geospatial signature. Similar to the altitude value comparison described above, there can be some ambiguity in the comparison of pressure values. For example, a user may be operating mobile computing device 105 near an entrance to the retail store at property location 110 and the pressure data sampled by mobile computing device 105 may be influenced by changes in pressure resulting from the entrance door being open nearby while other patrons enter or exit the retail store. Accordingly, a determination that the difference between the baseline pressure data of the geospatial profile and the pressure data of the geospatial signature exceeds a second predetermined threshold is followed up with a comparison of the pressure data of the geospatial signature and the predetermined pressure range of the baseline geospatial profile as described in more detail below.

If mobile computing device 105 determines that either of the first or second predetermined thresholds have been exceeded based upon the comparisons above, mobile computing device 105 determines whether pressure data of the geospatial signature is outside of the predetermined pressure range of the baseline geospatial profile. As discussed above, the predetermined pressure range can include a range of barometric or atmospheric pressure values corresponding to property location 110 on a given day that are offset to account for a known relative difference in pressure between indoors and outdoors due to the operation of climate control systems. Accordingly, a determination that the pressure data of the geospatial signature is outside of the predetermined pressure range of the baseline geospatial profile can confirm that mobile computing device 105 has been undesirably removed from property location 110, and mobile computing device 105 then enters the second operational mode.

Mobile computing device 105 performs one or more actions upon entering the second operational mode. In some embodiments, mobile computing device 105 creates an alert indicating that it has been taken from property location 110. Mobile computing device 105 can format an alert for transmission as one or more of an SMS message, an instant message generated, formatted and transmitted according to the IMESSAGE protocol, an email, or other message format for sending data electronically. The alert can include one or more of a unique device identifier of the mobile computing device, a time stamp indicating when the mobile computing device entered the second operational mode and the altitude and pressure data when mobile computing device 105 entered the second operational mode. Mobile computing device 105 can transmit the alert to another computing device (e.g., local server computing device 120, remote server computing device 140) via a wireless network connection (e.g., mobile network 130, communications network 125). In some embodiments, mobile computing device 105 periodically sends alerts including GPS coordinates it obtains from GPS satellites 135.

In some embodiments, upon entering the second operational mode mobile computing device 105 locks or ends any user sessions that have been established on mobile computing device 105, or prompts the user to enter user credential information. In some examples, mobile computing device 105 generates an audible alarm using speaker 240. Mobile computing device 105 can also generate a visual alarm using display 225 or light source 235. For example, mobile computing device 105 can cause a message to be displayed on display 225 indicating that mobile computing device 105 has been improperly taken from property location 110, and can further operate light source 235 in a manner intended to attract attention to mobile computing device 105 (e.g., pulsing, flashing, strobing). In some embodiments, upon entering the second operational mode mobile computing device 105 erases the contents of some or all of its volatile and non-volatile memory in order to preserve the confidentiality of any user data that may be stored on mobile computing device 105.

FIG. 4 is a flow diagram of a method 400 for detecting a proximity of mobile computing device 105 based upon physical properties of the property location where mobile computing device 105 is located, using the system 100 of FIG. 1. Mobile computing device 105 generates (405) a baseline proximity profile including data corresponding to at least three properties of a location of mobile computing device 105. In some embodiments, mobile computing device 105 generates a baseline proximity profile at a predetermined interval (e.g., once per day, once per week). In some embodiments, mobile computing device 105 generates a baseline proximity profile upon power up or restart of mobile computing device 105. In some embodiments, mobile computing device generates a baseline proximity profile upon the termination of a user session.

To generate the baseline proximity profile, mobile computing device 105 obtains sensor data from a plurality of sensors 215. This data can serve as the baseline against which later-sampled data is compared according to method 400. Mobile computing device 105 can obtain first baseline data from a first sensor responsive to a first property of property location 110. For example, the first sensor can be a 3-axis magnetometer, responsive to a change in the strength of a magnetic field at property location 110. The magnetometer can measure the strength of Earth's magnetic field and can detect changes in the magnetic field caused by other influences (e.g., electromagnetic security system, speaker, electric motor). Mobile computing device 105 can obtain second baseline data from a second sensor responsive to a second property of property location 110. For example, the second sensor can be a sound transducer responsive to a change in one or more properties of the sound at property location 110 such as sound amplitude, a sound tone, and a sound pitch. Mobile computing device 105 can obtain third baseline data from a third sensor responsive to a third property of property location 110. For example, the third sensor can be a light sensor responsive to a change in a property of the light at property location 110 such a change in a plurality of wavelengths of light or an intensity of light.

Generating the baseline geospatial profile can further include determining a baseline luminance based upon the third baseline data from the light sensor. In some embodiments, the baseline luminance is determined by multiplying the red, green, and blue components of the sampled light data by corresponding constants and summing the result. For example, luminance can be determined based on the equation $L=0.2126*R+0.7152*G+0.0722*B$, where L is luminance, and R, G and B are numeric values corresponding to red, green and blue components of the sampled light. Finally, mobile computing device 105 can generate a baseline proximity profile data structure including the first baseline data, the second baseline data, and the baseline luminance.

After generating the baseline geospatial profile, mobile computing device 105 enters (410) a first operational mode. The first operational mode can permit a user to establish a user session on the mobile computing device. The first operational mode can be substantially similar to the first operational mode described above with regard to method 300.

Upon entering the first operational mode, mobile computing device 105 obtains (415) first sensor data from the first sensor, obtains (420) second sensor data from the second sensor, and obtains (425) third sensor data from the third sensor. As discussed above, the first, second, and third sensors can each be responsive to a different property of property location 110 that are detectable by sensors 215 of mobile computing device 105. In some examples, the first sensor data represents the strength of a magnetic field at property location 110, the second sensor data represents properties of the sound at property location 110 such as sound amplitude, a sound tone, and a sound pitch, and the third sensor data represents properties of the light at property location 110 such as a plurality of wavelengths of light or an intensity of light. In some embodiments, mobile computing device 105 obtains data from sensors 215 at predetermined intervals of time (e.g., every 3 seconds).

Mobile computing device 105 generates (430) a proximity signature based upon the first sensor data, the second sensor data, and the third sensor data obtained at steps 415, 420 and 425, respectively. To generate the proximity signature, mobile computing device 105 determines a luminance based upon the third sensor data. Determining the luminance can be done using a substantially similar process as described above with respect to determining the baseline luminance. After determining the luminance, mobile computing device 105 generates a proximity signature data structure comprising the first sensor data, the second sensor data, and the luminance. In some embodiments, the data values of the proximity signature are formatted to facilitate comparison of the sensor data and luminance values with their counterparts in the baseline proximity profile. For example, the values of the proximity signature can be formatted to use same degree of precision and units of measurement as the values in the baseline proximity profile.

Mobile computing device 105 enters (440) a second operational mode if a difference between one or more corresponding values of the baseline proximity profile and the proximity signature exceeds a predetermined threshold. Mobile computing device 105 performs a plurality of operations to determine whether to enter the second operational mode. For example, mobile computing device 105 determines whether a difference between the first baseline data and the first sensor data exceeds a first predetermined threshold. In some embodiments, the first predetermined threshold is exceeded when the percent change between the first baseline data and the first sensor data is greater than 40%.

In some embodiments, the first baseline data and the first sensor data are obtained from a magnetometer. The first baseline data is obtained while mobile computing device 105 is within the retail store at property location 110 and represents the strength of the Earth's magnetic field at property location 110 (generally around 30-60 microteslas) along with contributions by other sources within the retail store (e.g., speakers, building wiring). As long as mobile computing device 105 remains within the retail store, the measured magnetic field is not expected to change significantly assuming the store layout remains somewhat static. Accordingly, detection of a difference between the first baseline data and the first sensor data that exceeds the first predetermined threshold can be an indication that mobile computing device 105 has been undesirably removed from property location 110.

Upon detecting that the difference between the first baseline data and the first sensor data exceeds the first predetermined threshold, mobile computing device 105 makes other determinations prior to entering the second operational mode. For example, mobile computing device 105 determines whether a difference between the second baseline data and the second sensor data exceeds a second predetermined threshold, and mobile computing device 105 determines whether a difference between the baseline luminance and the luminance calculated based upon the third sensor data exceeds a third predetermined threshold.

In some embodiments, the second baseline data and the second sensor data are obtained from a sound transducer (e.g., microphone). The second baseline data is obtained while mobile computing device 105 is within the retail store at property location 110 and represents properties of the sound within the retail store under typical conditions (e.g., sound level based on typical number of patrons at property location 110, typical volume of music or other audible track being played at property location 110). In some embodiments, the typical sound intensity level within the retail store is between 0 dB and 60 dB. A change between the typical measured sound intensity value (e.g., second baseline data) and a later-sampled sound intensity value (e.g., second sensor data) can indicate that mobile computing device 105 has been placed in a backpack or bag (e.g., decrease in sound intensity), or that mobile computing device 105 has been taken outside of the retail store at property location 110 (e.g., increase or decrease in sound intensity). In some embodiments, mobile computing device 105 enters the second operational mode if the percent change in value between the second baseline data and the second sensor data is greater than 40%.

The baseline luminance is computed based on the third baseline data which is obtained while mobile computing device 105 is within the retail store at property location 110 and represents properties of the light within the retail store such as a wavelength of light or intensity of light. A change between the typical measured luminance value (e.g., baseline luminance) and a later-sampled luminance value (e.g., the luminance calculated based upon the third sensor data data) can indicate that mobile computing device 105 has been placed in a backpack or bag (e.g., decrease in luminance), or that mobile computing device 105 has been taken outside of the retail store at property location 110 (e.g., increase or decrease in luminance). In some embodiments, mobile computing device 105 enters the second operational mode if the percent change in value between the baseline luminance and the luminance calculated based upon the third sensor data is greater than 50%.

Upon entering the second operational mode, mobile computing device 105 can perform substantially similar actions to those described above in relation to method 300. In some embodiments, the alert includes one or more of magnetic field data, sound data, and light data captured near or at the time mobile computing device 105 entered the second operational mode.

Accordingly, the methods and systems described herein are capable of monitoring the movement of mobile computing devices, and protecting sensitive and confidential information stored on mobile computing devices and displayed on mobile computing devices during user sessions.

The above-described techniques can be implemented in digital and/or analog electronic circuitry, or in computer hardware, firmware, software, or in combinations of them. The implementation can be as a computer program product, i.e., a computer program tangibly embodied in a machine-readable storage device, for execution by, or to control the operation of, a data processing apparatus, e.g., a programmable processor, a computer, and/or multiple computers. A computer program can be written in any form of computer or programming language, including source code, compiled code, interpreted code and/or machine code, and the computer program can be deployed in any form, including as a stand-alone program or as a subroutine, element, or other unit suitable for use in a computing environment. A computer program can be deployed to be executed on one computer or on multiple computers at one or more sites. The computer program can be deployed in a cloud computing environment (e.g., Amazon® AWS, Microsoft® Azure, IBM®).

Method steps can be performed by one or more processors executing a computer program to perform functions of the invention by operating on input data and/or generating output data. Method steps can also be performed by, and an apparatus can be implemented as, special purpose logic circuitry, e.g., a FPGA (field programmable gate array), a FPAA (field-programmable analog array), a CPLD (complex programmable logic device), a PSoC (Programmable System-on-Chip), ASIP (application-specific instruction-set processor), or an ASIC (application-specific integrated circuit), or the like. Subroutines can refer to portions of the stored computer program and/or the processor, and/or the special circuitry that implement one or more functions.

Processors suitable for the execution of a computer program include, by way of example, special purpose microprocessors specifically programmed with instructions executable to perform the methods described herein, and any one or more processors of any kind of digital or analog computer. Generally, a processor receives instructions and data from a read-only memory or a random access memory or both. The essential elements of a computer are a processor for executing instructions and one or more memory devices for storing instructions and/or data. Memory devices, such as a cache, can be used to temporarily store data. Memory devices can also be used for long-term data storage. Generally, a computer also includes, or is operatively coupled to receive data from or transfer data to, or both, one or more mass storage devices for storing data, e.g., magnetic, magneto-optical disks, or optical disks. A computer can also be operatively coupled to a communications network in order to receive instructions and/or data from the network and/or to transfer instructions and/or data to the network. Computer-readable storage mediums suitable for embodying computer program instructions and data include all forms of volatile and non-volatile memory, including by way of example semiconductor memory devices, e.g., DRAM, SRAM, EPROM, EEPROM, and flash memory devices; magnetic disks, e.g., internal hard disks or removable disks; magneto-optical disks; and optical disks, e.g., CD, DVD, HD-DVD, and Blu-ray disks. The processor and the memory can be supplemented by and/or incorporated in special purpose logic circuitry.

To provide for interaction with a user, the above described techniques can be implemented on a computing device in communication with a display device, e.g., a CRT (cathode ray tube), plasma, or LCD (liquid crystal display) monitor, a mobile computing device display or screen, a holographic device and/or projector, for displaying information to the user and a keyboard and a pointing device, e.g., a mouse, a trackball, a touchpad, or a motion sensor, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, and/or tactile input.

The above-described techniques can be implemented in a distributed computing system that includes a back-end component. The back-end component can, for example, be a data server, a middleware component, and/or an application server. The above described techniques can be implemented in a distributed computing system that includes a front-end component. The front-end component can, for example, be a client computer having a graphical user interface, a Web browser through which a user can interact with an example implementation, and/or other graphical user interfaces for a transmitting device. The above described techniques can be implemented in a distributed computing system that includes any combination of such back-end, middleware, or front-end components.

The components of the computing system can be interconnected by transmission medium, which can include any form or medium of digital or analog data communication (e.g., a communication network). Transmission medium can include one or more packet-based networks and/or one or more circuit-based networks in any configuration. Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), Bluetooth, near field communications (NFC) network, Wi-Fi, WiMAX, general packet radio service (GPRS) network, HiperLAN), and/or other packet-based networks. Circuit-based networks can include, for example, the public switched telephone network (PSTN), a legacy private branch exchange (PBX), a wireless network (e.g., RAN, code-division multiple access (CDMA) network, time division multiple access (TDMA) network, global system for mobile communications (GSM) network), and/or other circuit-based networks.

Information transfer over transmission medium can be based on one or more communication protocols. Communication protocols can include, for example, Ethernet protocol, Internet Protocol (IP), Voice over IP (VOIP), a Peer-to-Peer (P2P) protocol, Hypertext Transfer Protocol (HTTP), Session Initiation Protocol (SIP), H.323, Media Gateway Control Protocol (MGCP), Signaling System #7 (SS7), a Global System for Mobile Communications (GSM) protocol, a Push-to-Talk (PTT) protocol, a PTT over Cellular (POC) protocol, Universal Mobile Telecommunications System (UMTS), 3GPP Long Term Evolution (LTE) and/or other communication protocols.

Devices of the computing system can include, for example, a computer, a computer with a browser device, a telephone, an IP phone, a mobile computing device (e.g., cellular phone, personal digital assistant (PDA) device, smart phone, tablet, laptop computer, electronic mail device), and/or other communication devices. The browser device includes, for example, a computer (e.g., desktop computer and/or laptop computer) with a World Wide Web browser (e.g., Chrome™ from Google, Inc., Microsoft® Internet Explorer® available from Microsoft Corporation, and/or Mozilla® Firefox available from Mozilla Corporation). Mobile computing device include, for example, a Blackberry® from Research in Motion, an iPhone® from Apple Corporation, and/or an Android™-based device. IP phones include, for example, a Cisco® Unified IP Phone 7985G and/or a Cisco® Unified Wireless Phone 7920 available from Cisco Systems, Inc.

Comprise, include, and/or plural forms of each are open ended and include the listed parts and can include additional parts that are not listed. And/or is open ended and includes one or more of the listed parts and combinations of the listed parts.

One skilled in the art will realize the subject matter may be embodied in other specific forms without departing from the spirit or essential characteristics thereof. The foregoing embodiments are therefore to be considered in all respects illustrative rather than limiting of the subject matter described herein.

What is claimed is:

1. A computerized method for detecting movement of a mobile computing device based upon geospatial data about a property location of the mobile computing device, the method comprising:
    generating, by a mobile computing device, a baseline geospatial profile comprising baseline pressure data, and a predetermined pressure range;
    entering, by the mobile computing device, a first operational mode, wherein the first operational mode permits a user to establish a user session on the mobile computing device;
    obtaining, by the mobile computing device, pressure data from a sensor responsive to a change in a pressure of the location of the mobile computing device;
    generating, by the mobile computing device, a geospatial signature based upon the pressure data; and
    comparing, by the mobile computing device, corresponding data values of the geospatial signature and the baseline geospatial profile.

2. The method of claim 1 wherein generating the baseline geospatial profile further comprises:
    obtaining, by the mobile computing device, GPS coordinate data from a GPS of the mobile computing device, the GPS coordinate data corresponding to a geographic location of the mobile computing device prior to entering the first operational mode;
    determining, by the mobile computing device, a property location of the mobile computing device based upon the GPS coordinate data;
    obtaining, by the mobile computing device, the baseline pressure data from the sensor prior to entering the first operational mode; and
    retrieving, by the mobile computing device from a server computing device, the predetermined pressure range, wherein the predetermined pressure range comprises a maximum pressure value and a minimum pressure value.

3. The method of claim 2 wherein the predetermined pressure range is based upon one of:
    historical pressure data corresponding to the property location of the mobile computing device retrieved from a server computing device; and
    currently forecasted pressure data corresponding to the property location of the mobile computing device retrieved from a server computing device.

4. The method of claim 1 further comprising entering, by the mobile computing device, a second operational mode upon determining the difference between corresponding data values of the geospatial signature and the baseline geospatial profile exceeds a predetermined threshold.

5. The method of claim 1 further comprising:
    determining, by the mobile computing device, a difference between the baseline pressure data and the pressure data; and
    entering, by the mobile computing device, a second operational mode upon determining the difference exceeds a predetermined threshold.

6. The method of claim 1 wherein the baseline geospatial profile further comprises baseline altitude data, the method further comprising:
    obtaining, by the mobile computing device, altitude data from an altitude sensor responsive to a change in altitude of the mobile computing device;
    determining, by the mobile computing device, the altitude data is less than the baseline altitude data; and
    entering, by the mobile computing device, a second operational mode upon determining the pressure data is outside of the predetermined pressure range.

7. The method of claim 1 wherein obtaining pressure data further comprises obtaining data from a hygrometer.

8. The method of claim 4 wherein entering the second operational mode comprises one or more of:
    transmitting, by the mobile computing device, an alert to a remote computing device;
    locking, by the mobile computing device, a user session that has been established on the mobile computing device;
    ending, by the mobile computing device, a user session that has been established on the mobile computing device;
    generating, by the mobile computing device, an audible alarm on a speaker of the mobile computing device;
    generating, by the mobile computing device, a visual alarm on one or more of a display and a light source of the mobile computing device;
    prompting, by the mobile computing device, the user to enter user credential information; or
    erasing, by the mobile computing device, the contents of a volatile and a non-volatile information storage of the mobile computing device.

9. The method of claim 8 wherein the alert comprises one or more of a unique device identifier of the mobile computing device, a time stamp indicating when the mobile computing device entered the second operational mode, and the pressure data.

10. The method of claim 8 wherein transmitting the alert further comprises formatting, by the mobile computing device, the alert for transmission as one or more of an SMS message, an instant message according to the IMESSAGE protocol, and an email, and an email.

11. A computer program product, tangibly embodied in a non-transitory computer readable storage device, for detecting movement of a mobile computing device based upon geospatial data about a property location of the mobile computing device, the computer program product including instructions operable to cause the mobile computing device to:
   generate a baseline geospatial profile comprising baseline pressure data, and a predetermined pressure range;
   enter a first operational mode, wherein the first operational mode permits a user to establish a user session on the mobile computing device;
   obtain pressure data from a sensor responsive to a change in a pressure of the location of the mobile computing device;
   generate a geospatial signature based upon the pressure data; and
   compare corresponding data values of the geospatial signature and the baseline geospatial profile.

12. The computer program product of claim 11 further comprising instructions operable to cause the mobile computing device to:
   obtain GPS coordinate data from a GPS of the mobile computing device, the GPS coordinate data corresponding to a geographic location of the mobile computing device prior to entering the first operational mode;
   determine a property location of the mobile computing device based upon the GPS coordinate data;
   obtain the baseline pressure data from the sensor prior to entering the first operational mode;
   retrieve, from a server computing device, the predetermined pressure range, wherein the predetermined pressure range comprises a maximum pressure value and a minimum pressure value.

13. The computer program product of claim 12 wherein the predetermined pressure range is based upon one of:
   historical pressure data corresponding to the property location of the mobile computing device retrieved from a server computing device; and
   currently forecasted pressure data corresponding to the property location of the mobile computing device retrieved from a server computing device.

14. The computer program product of claim 11 further comprising instructions operable to cause the mobile computing device to enter a second operational mode upon determining the difference between corresponding data values of the geospatial signature and the baseline geospatial profile exceeds a predetermined threshold.

15. The computer program product of claim 11 further comprising instructions operable to cause the mobile computing device to:
   determine a difference between the baseline pressure data and the pressure data; and
   enter a second operational mode upon determining the difference exceeds a predetermined threshold.

16. The computer program product of claim 11 wherein the baseline geospatial profile further comprises baseline altitude data, the computer program product further comprising instructions operable to cause the mobile computing device to:
   obtain altitude data from an altitude sensor responsive to a change in altitude of the mobile computing device;
   determine the altitude data is less than the baseline altitude data; and
   enter a second operational mode upon determining the pressure data is outside of the predetermined pressure range.

17. The computer program product of claim 11 wherein obtaining pressure data further comprises obtaining data from a hygrometer.

18. The computer program product of claim 14 further comprising instructions operable to cause the mobile computing device to perform one or more of:
   transmit an alert to a remote computing device;
   lock a user session that has been established on the mobile computing device;
   end a user session that has been established on the mobile computing device;
   generate an audible alarm on a speaker of the mobile computing device;
   generate a visual alarm on one or more of a display and a light source of the mobile computing device;
   prompt the user to enter user credential information; or
   erase the contents of a volatile and a non-volatile information storage of the mobile computing device.

19. The computer program product of claim 18 wherein the alert comprises one or more of a unique device identifier of the mobile computing device, a time stamp indicating when the mobile computing device entered the second operational mode, and the pressure data.

20. The computer program product of claim 18 further comprising instructions operable to cause the mobile computing device to format the alert for transmission as one or more of an SMS message, an instant message according to the IMESSAGE protocol, and an email, and an email.

* * * * *

UNITED STATES PATENT AND TRADEMARK OFFICE
CERTIFICATE OF CORRECTION

PATENT NO. : 10,015,626 B2
APPLICATION NO. : 15/606564
DATED : July 3, 2018
INVENTOR(S) : Madhani Page 1 of 1

It is certified that error appears in the above-identified patent and that said Letters Patent is hereby corrected as shown below:

In the Claims

At Line 5 of Claim 10 (Column 19, Line 8), delete "and an email, and an email." and insert --and an email.--

At Line 5 of Claim 20 (Column 20, Line 52), delete "and an email, and an email." and insert --and an email.--

Signed and Sealed this
Twenty-fifth Day of September, 2018

Andrei Iancu
*Director of the United States Patent and Trademark Office*